(12) United States Patent
Shoeb et al.

(10) Patent No.: US 10,070,807 B2
(45) Date of Patent: Sep. 11, 2018

(54) DETECTION AND EVALUATION OF USER GRIP WITH A HANDHELD TOOL

(71) Applicant: VERILY LIFE SCIENCES LLC, Mountain View, CA (US)

(72) Inventors: Ali Shoeb, Mill Valley, CA (US); Anupam Pathak, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 238 days.

(21) Appl. No.: 14/842,707

(22) Filed: Sep. 1, 2015

(65) Prior Publication Data

US 2017/0055885 A1   Mar. 2, 2017

(51) Int. Cl.
*A61B 1/24* (2006.01)
*A63B 23/16* (2006.01)
(Continued)

(52) U.S. Cl.
CPC ............ *A61B 5/1125* (2013.01); *A47G 21/02* (2013.01); *A61B 5/1101* (2013.01); *A61B 5/225* (2013.01); *A61B 5/486* (2013.01); *A61B 5/4836* (2013.01); *A61B 5/6887* (2013.01); *A61B 5/7264* (2013.01); *A61B 5/7282* (2013.01); *G01L 5/00* (2013.01); *G16H 50/20* (2018.01); *A47G 2200/046* (2013.01); *A61B 5/0022* (2013.01);
(Continued)

(58) Field of Classification Search
None
See application file for complete search history.

(56) References Cited

U.S. PATENT DOCUMENTS 5,904,639 A  * 5/1999 Smyser .................. A61B 5/225
                                                                482/1
6,962,569 B2 * 11/2005 Smyser .................. A61B 5/225
                                                                600/595
(Continued)

FOREIGN PATENT DOCUMENTS

CN       103431850 A     12/2013
JP      2010-023593 A     2/2010
(Continued)

OTHER PUBLICATIONS

PCT/US2016/045377—International Search Report and Written Opinion, dated Nov. 14, 2016, 12 pages.
(Continued)

*Primary Examiner* — Peter Macchiarolo
*Assistant Examiner* — Jermaine Jenkins
(74) *Attorney, Agent, or Firm* — Christensen O'Connor; Johnson Kindness PLLC

(57) ABSTRACT

Techniques and mechanisms for detecting and evaluating grip by a user operating a handheld tool. In an embodiment, the tool includes a handle, one or more pressure sensors disposed in or on the handle, and an attachment arm. An output from the one or more sensors is generated while a user-assistive device is coupled to a distal end of an attachment arm of the tool. Logic of the tool calculates a grip metric based on the sensor output, and the tool transmits, based on the grip metric, a signal including medical diagnostic information. In another embodiment, the user-assistive device includes a utensil attachment or a personal hygiene attachment.

24 Claims, 5 Drawing Sheets

(51) Int. Cl.
*A61B 5/11* (2006.01)
*G01L 5/00* (2006.01)
*A61B 5/00* (2006.01)
*A61B 5/22* (2006.01)
*A47G 21/02* (2006.01)
*G16H 50/20* (2018.01)

(52) U.S. Cl.
CPC ..... *A61B 5/4082* (2013.01); *A61B 2560/0475* (2013.01); *A61B 2562/04* (2013.01)

(56) References Cited

U.S. PATENT DOCUMENTS

| | | | |
|---|---|---|---|
| 7,412,883 | B2 | 8/2008 | Krullaards |
| 7,448,265 | B2* | 11/2008 | Smyser ................. A61B 5/225 73/379.02 |
| 7,470,217 | B2* | 12/2008 | Jones-Glaser ..... A63B 21/0085 482/49 |
| 7,739,910 | B2* | 6/2010 | Clem ................. A63B 21/0004 73/379.02 |
| 2002/0156381 | A1 | 10/2002 | Kao et al. |
| 2009/0025475 | A1* | 1/2009 | DeBeliso ............... A61B 5/225 73/379.02 |
| 2010/0240962 | A1* | 9/2010 | Contant ................. A47G 21/02 600/300 |
| 2013/0060124 | A1 | 3/2013 | Zietsma |
| 2013/0297022 | A1 | 11/2013 | Pathak |

FOREIGN PATENT DOCUMENTS

| | | |
|---|---|---|
| KR | 101138249 B1 | 4/2012 |
| KR | 2012-107801 A | 10/2012 |
| WO | WO 01/45561 A1 | 6/2001 |
| WO | WO 2004/045723 A1 | 6/2004 |

OTHER PUBLICATIONS

U.S. Appl. No. 14/627,893, filed Feb. 20, 2015, Pathak et al.
U.S. Appl. No. 14/746,649, filed Jun. 22, 2015, Pathak et al.

* cited by examiner

DETECTION AND EVALUATION OF USER GRIP WITH A HANDHELD TOOL

BACKGROUND

1. Technical Field

This disclosure relates generally to diagnostic functionality provided by a tool, and in particular but not exclusively, relates to the detection and evaluation of grip pressure by a user of a handheld tool.

2. Background Art

Muscular disorders are often caused by chronic neurodegenerative diseases such as Parkinson's Disease ("PD") and Essential Tremor ("ET"). Many disorders can be severe enough to cause a significant degradation in quality of life, interfering with daily activities/tasks such as eating, drinking, or writing. Such conditions are often incurable, but their progression can be mitigated if early detection is made.

Clinical research suggests that an increasing severity of Parkinson's disease, for example, is indicated by a patient's weakening hand grip. However, clinical diagnosis currently provides little in the way of monitoring to detect for variations in grip strength over time. Grip is typically only assessed qualitatively while a patient is in a clinic in the presence of a physician. Such assessment requires a clinical visit that, due to its subjective nature during a brief period of time, is often prone to errors or intra-clinician variability. Patients' self-reporting is also highly subjective and prone to error. This creates significant challenges when developing and evaluating long-term treatments or interventions for these diseases.

BRIEF DESCRIPTION OF THE DRAWINGS

The various embodiments of the present invention are illustrated by way of example, and not by way of limitation, in the figures of the accompanying drawings and in which.

DETAILED DESCRIPTION

Embodiments of an apparatus, system and process for detecting and evaluating grip by a user operating a handheld tool are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Certain embodiments variously provide for a tool to detect that a test is being (or is to be) performed, where the test is to evaluate grip strength based on sensor data generated with the tool and, in some embodiments, based on reference information that, for example, describes one or more diagnostic test criteria. Based on processing of the sensor data, grip metric information may be generated and, in some embodiments, communicated from the tool to provide for clinical evaluation of the—e.g., wherein the information indicates weak grip, tremor and/or any of various other conditions that, in turn, may indicate a state of a neuromuscular (or other) disorder. In some embodiments, grip analysis information may be used in a learning algorithm to improve operation of the handheld tool by the user.

Figure 1A:
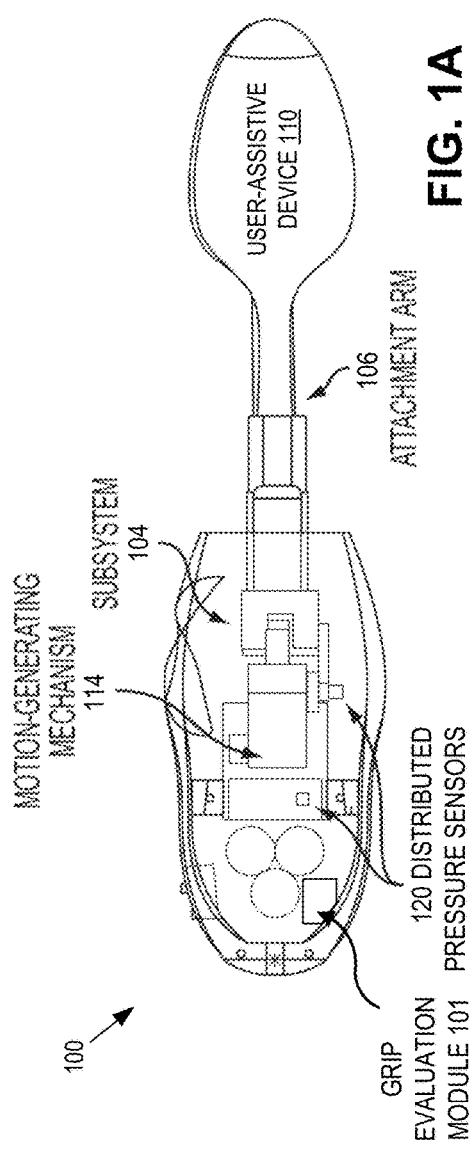
FIG. 1A is a cross-sectional illustration of a handheld tool that evaluates user grip, in accordance with an embodiment of the disclosure.
Figure 1B:
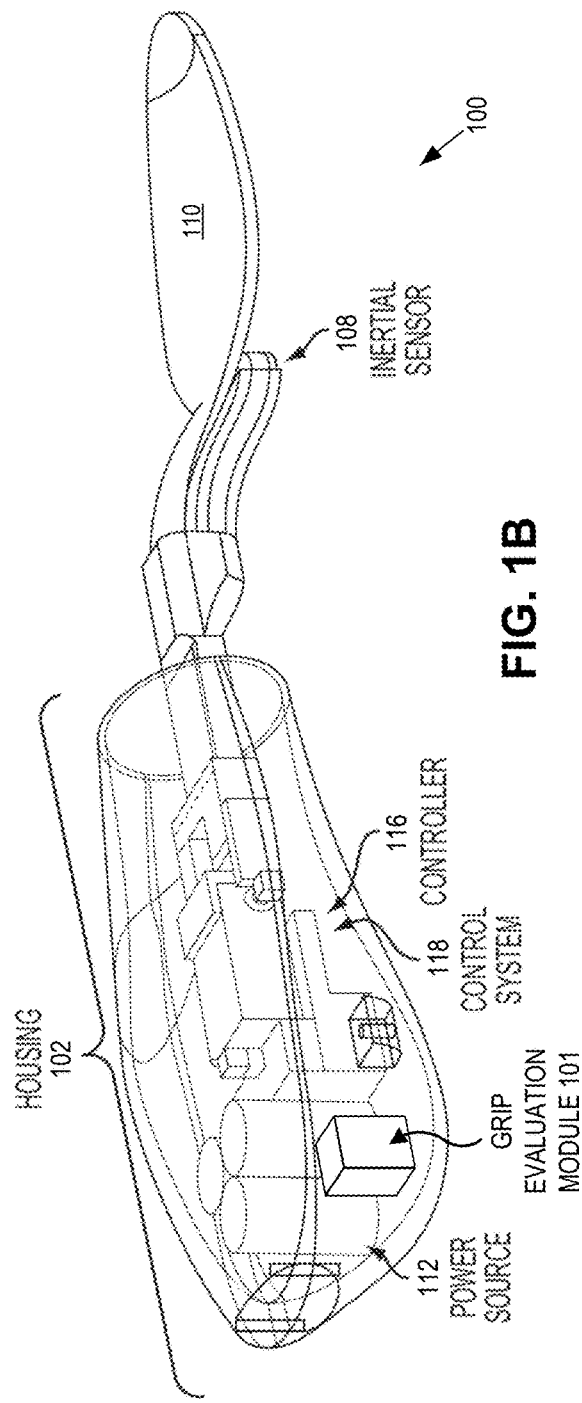
FIG. 1B is a perspective view illustration of the handheld tool that evaluates user grip, in accordance with an embodiment of the disclosure.

FIGS. 1A and 1B illustrate a handheld tool 100 that, in accordance with an embodiment of the disclosure, detects a pressure exerted by a user and, in some embodiments, further evaluates a metric of user grip based on such pressure. Diagnosis information based on the grip metric may be communicated from the tool—e.g., via a wired network and/or a wireless network—to a computer of a physician, hospital, clinic or other remote agent. FIG. 1A is a cross-sectional illustration of handheld tool 100 while FIG. 1B is a perspective view illustration of the same. Handheld tool 100 may also be capable of detecting and compensating for unintentional muscle movement (tremors); however, it should be appreciated that various embodiments need not include the mechanisms and associated sensors for tremor compensation, even though both features are incorporated into the illustrated embodiment of handheld tool 100. Accordingly, the illustrated embodiment of handheld tool 100 may include a subsystem for detecting pressure, applied by a user, and a subsystem for detecting tremors indicated (for example) by variation in such pressure. These subsystems may have distinct components, or share some components such as power systems, memory, a controller, and may even share one or more sensors. In some embodiments, some or all components of a subsystem to detect and/or compensate for tremors may be omitted.

Handheld tool 100 may include a housing 102, which functions as a handle for a user to hold handheld tool 100. Handheld tool 100 may also include an attachment arm 106 coupled to the housing 102. Attachment arm 106 is configured to accept a user-assistive device 110 (e.g., a spoon in the illustrated embodiment) to its end distal from housing 102. In another embodiment, a user-assistive device is integrated with or otherwise permanently attached to housing 102. For example, attachment arm 106 may alternatively be integrated with a specific type of user-assistive device 110 (spoon illustrated). In other embodiments, attachment arm 106 can variously receive one or more different user-assistive devices 110 in a variety of ways including but not limited to a friction, snap, or other form of locking mechanism.

Handheld tool 100 may further include a grip evaluation module ("GEM") 101 for calculating a value of a grip metric and, in some embodiments, perform an evaluation based on the grip metric value and reference information including, for example, one or more threshold values of a diagnostic test criteria. One or more components of GEM 101 may be disposed within housing 102 to measure and track grip pressure (e.g., including measuring lack of pressure) applied to the handle that the user holds. FIGS. 1A and 1B illustrate GEM 101 as a single block within housing 102; however, in other embodiments, GEM 101 includes several functional items that may assume a variety of different form factors and may further be spread throughout housing 102.

The illustrated embodiment of handheld tool 100 further includes a subsystem 104 to detect motion of user-assistive device 110. Subsystem 104 may include at least one inertial sensor (not shown) placed, for example, along attachment arm 106 to measure absolute movement of attachment arm 106 and user-assistive device 110. Subsystem 104 may further include a portable power source 112, a control system 118, and distributed motion sensors 120 for measuring pressure applied to housing 102. Portable power source 112 may utilize a variety of options including but not limited to a rechargeable battery, a solar panel, etc. As mentioned above, GEM 101 may share one or more of the components of subsystem 104 (e.g., power source 112, controller 116, etc.). In the illustrated embodiment of handheld tool 100, subsystem 104 further comprises a motion-generating mechanism 114 to compensate for user tremors. However, in other embodiments, one or more of the components of subsystem 104 to compensate tremor motions may also be omitted (e.g., controller 116, motion-generating mechanism 114, etc.) while still implementing the grip pressure detection and evaluation functionality disclosed herein.

One or more sensors of handheld tool 100—e.g., including the illustrative distributed pressure sensors 120—may variously generate sensor data indicating pressure applied to handheld tool 100 by a user. The particular number, positioning and/or types of such sensors 120 is merely illustrative, and not limiting on some embodiments. To detect user grip according to an embodiment, a pressure applied to housing 102 may be sensed. For this sensing, the at least one pressure sensor 120 may be placed on or under a surface of housing 102 and may be used to measure pressure applied during performance of an everyday task with tool 100 or, in some embodiments, during a test phase wherein the user is prompted to apply a grip pressure to housing 102. The distributed sensors 120 may include any of a variety of one or more capacitive, piezoresistive, piezoelectric and/or other mechanisms adapted from conventional pressure sensing techniques. The distributed motion sensors 120 may include, for example, at least one Hall-effect pressure sensor, although certain embodiments are not limited in this regard.

Information representing the sensed pressure applied to handheld tool 100 may be provided by the sensors directly or indirectly to GEM 101—e.g., via control system 118—for processing to determine whether a characteristic of user grip satisfies one or more criteria of a pre-defined test for evaluating a neurological (or other) medical condition. For example, GEM 101 may include or otherwise have access to a memory (not shown) storing reference information that includes respective definitions of one or more diagnostic tests. In an embodiment, a test definition describes one or more threshold levels each for a respective characteristic (e.g., including force, rate of change, frequency of tremor and/or the like) of user grip. Based on sensor data and a test definition, GEM 101 may perform processing to determine whether a characteristic of grip applied to handheld tool 100 qualifies (e.g., according to some pre-defined criteria) as being indicative of a particular state of a corresponding medical condition. In some embodiments, such diagnostic processing (and/or other evaluation of user grip) is performed by a device remote from handheld tool 100 based on grip metric information that handheld tool 100 sends to the remote agent.

In an embodiment where tremor compensation functionality is provided, control system 118 may send voltage commands, in response to sensors 120, to motion-generating mechanism 114 through controller 116 to cancel or otherwise mitigate the user's tremors or unintentional muscle movements. This cancellation may maintain and stabilize a position of the user-assistive device 110, keeping it centered relative to the housing 102. In one embodiment, controller 116 comprises an electrical system capable of producing an electrical response from sensor inputs such as a programmable microcontroller a field-programmable gate array (FPGA), an application specific integrated circuit ("ASIC"), or otherwise. In one embodiment, the control system 118 is a closed-loop control system that senses motion and acceleration at various points along handheld tool 100 and feeds detailed information into a control algorithm that moves motion-generating mechanism 114 appropriately to cancel the net effect of a user's unintentional muscle movements and thus stabilize the position of user-assistive device 110.

One of ordinary skill in the art will readily recognize that an apparatus, a system, or method as described herein may be utilized for a variety of applications. For example, various different user-assistive devices 110 may include a manufacturing tool, a surgical tool, a kitchen utensil (e.g., fork, knife, spoon), a sporting tool, a yard tool, a grooming tool (e.g., comb, nail clippers, tweezers, make-up applicator, etc.), or a dental hygiene tool (e.g., toothbrush, flossing tool, etc.). Thus, handheld tool 100 may be useful in improving the quality of life for the multitudes of individuals suffering from neurological disorders.

Figure 2:
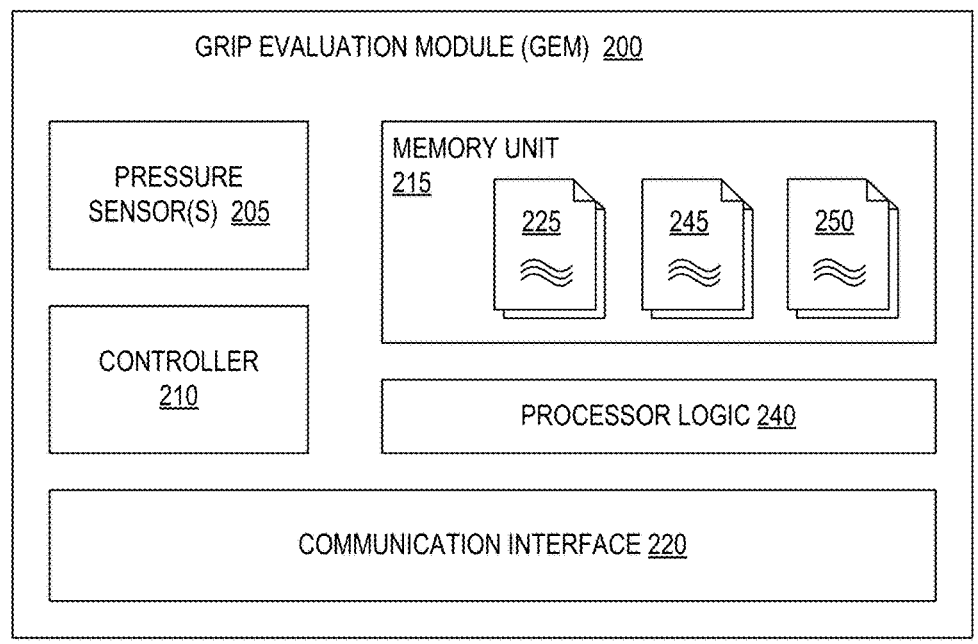
FIG. 2 is a functional block diagram illustrating a module to detect and evaluate user grip, in accordance with an embodiment of the disclosure.
Figure 2:
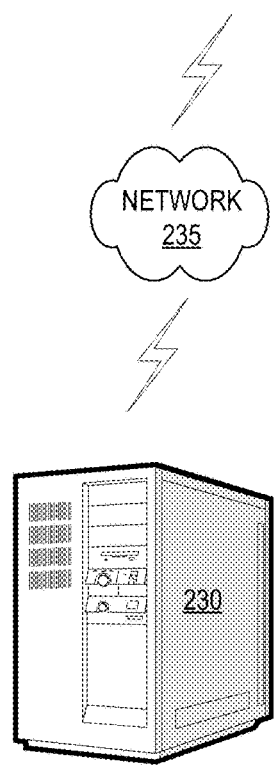

FIG. 2 is a functional block diagram illustrating a grip evaluation module (GEM) 200, in accordance with an embodiment of the disclosure. GEM 200 is one possible implementation of GEM 101 illustrated in FIGS. 1A and 1B, for example. The illustrated embodiment of GEM 200 includes one or more pressure sensors 205, a controller 210, a memory unit 215, a communication interface 220 and processor logic 240.

One or more pressure sensors 205 may be disposed in rigid contact with housing 102 (or other such handle structure) to directly measure pressure applied to a handle and by extension the grip pressure of a user's hand. GEM 200 facilitates the measurement of user grip during a test and/or while the user is performing an everyday task, such as eating, brushing teeth or grooming (e.g., applying makeup). This is an important distinction over conventional in-clinic evaluations that subjectively assess the grip pressure of a hand while a patient is attempting to perform a task in a time-limited and artificial environment. Measurement and tracking of grip pressure while the patient is performing an everyday task measures the condition under real-world scenarios that are most adversely impacted by neurological conditions. Accordingly, GEM 200 may be embedded within everyday items or tools that are used routinely by patients to accurately measure and track their condition. This can lead to improved evaluations.

Not only can handheld tool 100 measure and track user grip during a test routine and/or during an everyday task, but it can conveniently do so over a period of time to obtain a more reliable dataset for statistical analysis. Furthermore, handheld tool 100 can be used at home where the user is more relaxed and under less stress than a formal evaluation in a practitioner's office. Data collection within the home environment along with larger datasets than can be obtained in-clinic, can provide more reliable data for evaluation of a patient's symptoms. Improved evaluation and diagnosis of a patient's movement disorder facilitate improved treatments and interventions of the various diseases and the conditions that cause human movement disorders.

One or more pressure sensors 205 may be implemented using any of a variety of capacitive, piezoelectric, piezoresistive, MEMS and/or other devices that measure grip pressure applied to the handle of handheld tool 100. In various embodiments, one or more pressure sensors 205 may include various combinations of some or all of the above listed pressure measuring devices. Furthermore, these pressure sensors may be disposed together on a common substrate that is within housing 102, or disposed throughout housing 102.

Controller 210 may be communicatively coupled to one or more pressure sensors 205 and memory unit 215 to read pressure data output from one or more pressure sensors 205 and store the pressure data into memory unit 215. The pressure data may be collected during a test routine and/or over a period of time. For example, the pressure data may be collected while the user performs an individual task—e.g., repeatedly over the course of an hour, a day, a week, or other period of time. The collected pressure data stored in memory unit 215 may form a log 225. In one embodiment, log 225 may contain enough information about the user's grip (force, duration, rate of change, frequency of grip pulses, etc.), based upon the pressure data output from one or more pressure sensors 205, to recreate those pressures using log 225. In one embodiment, log 225 may also record date/time stamps of when various pressure data was collected.

Information in log 225 may be evaluated, based on reference data, to determine whether a characteristic of grip represented by such information is indicative of a state of a medical condition that corresponds to some pre-defined diagnostic test. GEM 200 may include or otherwise have access to reference data 245—e.g., in memory unit 215—that includes respective definitions of one or more diagnostic tests. An evaluation based on log 225 and reference data 245 may be performed—e.g., by processor logic 240 of GEM 200—to determine whether a grip pressure characteristic detected by one or more pressure sensors 205 meets some pre-defined test criteria to qualify as an instance of a particular state of a medical condition. For example, the test definition may identify one or more threshold levels of a grip characteristic, where processor logic 240—e.g., including hardware, firmware and/or executing software—calculates some metric of conformity to the one or more characteristics. Such a metric may be compared to a threshold level of conformity, where based on such comparison, processor logic 240 signals that an associated state of a medical condition is indicated. In another embodiment, processor logic 240 (or other logic responsive thereto) may instead prepare data in log 225 for communication to a remote agent, where the remote agent is to perform such diagnostic testing.

In some embodiments, identifying a state of a medical condition is further based on context information (not shown)—e.g., other than information specifying a characteristic of user grip—that is included in memory unit 215 or is otherwise available to processor logic 240. By way of illustration and not limitation, such context information may identify where (e.g., in a particular room or other geographic location) and/or when (e.g., at a particular date, day of the week and/or time of day) a particular user can be expected to operate a tool that includes GEM 200. Alternatively or in addition, such context information may include user profile information describing a history of previous operation of the tool by the user. In some embodiments, context information identifies a particular type of user-assistive device 110 that was attached to the handheld 100 when the grip metric data was collected. Alternatively or in addition, context information may include or otherwise be based on an input from a user explicitly specifying that gripping of the tool by the user has been, is being or will be performed. Certain embodiments are not limited with respect to a particular source of and/or delivery mechanism for such context information, which may be provided, for example, as an a priori input to GEM 200.

Such context information may directly or indirectly provide an indication of an action of a task (e.g., eating with a fork, knife, or spoon, etc.) being performed by the user when grip pressure data was collected. For example, based on a context that coincides with motion detected by one or more pressure sensors 205, processor logic 240 may identify a task (or a particular action of a task) as being more closely associated with the context—e.g., as compared to some other task or action of a task. In response, processor logic 240 may select or otherwise identify such a task (or action thereof) as being more likely to correspond to a grip characteristic coinciding with the context.

Controller 210 and/or processor logic 240 may be implemented with a programmable microcontroller, a FPGA, an ASIC or other devices capable of executing logical instructions. The logical instructions themselves may be hardware logic, software logic (e.g., stored within memory unit 215 or elsewhere), or a combination of both. Memory unit 215 may be implemented using volatile or non-volatile memory (e.g., flash memory), in one embodiment.

Communication interface 220 may be communicatively coupled to output the motion log 225 from memory unit 215 to remote server 230 via network 235 (e.g., the Internet). In one embodiment, communication interface 220 is a wireless communication interface (e.g., Bluetooth, WiFi, etc.). For example, communication interface 220 may establish a wireless link to a user's cellular phone which delivers, to server 230 via an installed grip detection and evaluation application, log 225 and/or evaluation results—e.g., the illustrative evaluation data 250—generated based on log 225 and reference information 245. The application may enable the user to control privacy settings, add comments about their usage of handheld tool 100, setup automatic periodic reporting of data, initiate a one-time reporting of data, along with other user functions. In yet another embodiment, communication interface 220 may be a wired communication port (e.g., USB port). For example, when the user connects handheld tool 100 to a charging dock to charge power source 112, communication interface 220 may also establish a communication session with remote server 230 for delivery of log 225 thereto.

Although some embodiments are not limited in this regard, communication interface 220 may additionally or alternatively include one or more audio, visual, haptic or other I/O mechanisms to prompt a user to perform a grip test to aid in medical diagnosis. By way of illustration, communication interface 220 may include a speaker and/or one or more light emitting diodes (LEDs) which processor logic 240 operates to indicate to the user that a particular grip test is to be performed. Alternatively or in addition, communication interface 220 may signal that one or more remote devices (not shown) are to provide such a prompt. In response, the user may perform any of various grip actions such as sustaining at least some threshold level of grip force for a defined period of time. Pressure sensors 205 may detect pressure imparted by the user during the performed one or more grip actions.

In the illustrative embodiment of FIG. 2, processor logic 240 and reference data 245 are features local to GEM 200. However, in another embodiment, processor logic 240 and reference data 245 instead reside in server 230 or some other device that is remote from a handheld tool which includes GEM 200. For example, GEM 200 may provide log 225 via network 235, where processing of the data of log 225 is performed to determine, remotely from GEM 200, whether a particular medical condition is indicated by a characteristic of grip applied to a handheld tool that includes GEM 200.

Figure 3:
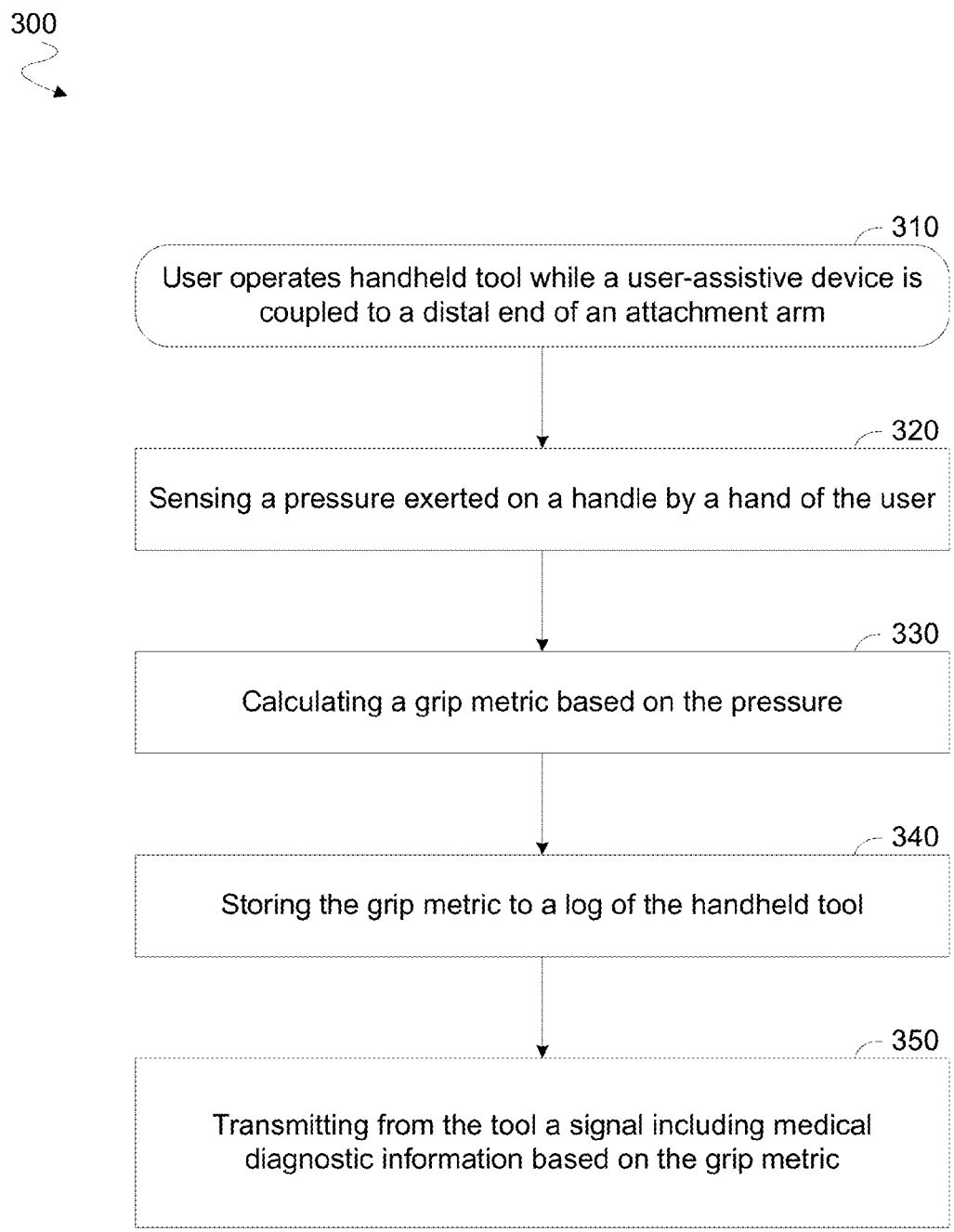
FIG. 3 is a flow chart illustrating a process to provide diagnostic evaluation of a user's grip using a handheld tool, in accordance with an embodiment of the disclosure.

FIG. 3 illustrates features of a method 300 for detecting and evaluating user grip with a handheld tool according to an embodiment. Method 300 may be performed based on sensor data generated with the handheld tool (such as handheld tool 100)—e.g., where the sensor data is generated while, at 310, a user operates the handheld tool having a user-assistive device (such as user-assistive device 116) coupled thereto. In certain embodiments, at least some of method 300 is performed by a computer device (e.g., server 230) that is remote from such a handheld tool, based on sensor data generated by the handheld tool.

Method 300 may include, at 320, sensing a pressure exerted on a handle of the tool by a hand of a user. The sensing at 320 may be performed based on an output from one or more sensor mechanisms of the handheld tool such as the distributed motion sensors 120. Method may further comprise, at 330, calculating a grip metric based on the pressure sensed at 320. The grip metric may specify or otherwise indicate one or more characteristics including, for example, a level of force of a grip, a rate of change of such force, a frequency of tremor in grip strength and/or the like. Alternatively or in addition, a grip metric may specify or otherwise indicate a time duration for a grip characteristic. Although certain embodiments are not limited in this regard, method 300 may further comprise, at 340, includes storing the grip metric to a log of the handheld tool. The storing at 340 may further include writing respective timestamp values for various grip metric values.

In an embodiment, method 300 further comprises, at 350, transmitting from the tool a signal including medical diagnostic information based on the grip metric. For example, method 300 may include one or more additional operations (not shown) to evaluate a grip metric based on one or more criteria of a diagnostic test to identify a medical condition. The evaluation may be based at least in part on the tool accessing reference data including a definition of a diagnostic test. In such an embodiment, the transmitting at 350 may include sending to a remote agent (e.g., a computer of a physician, hospital, clinic, etc.) a result of such an evaluation. Alternatively, the transmitting at 350 may include sending one or more grip metrics to the remote agent, wherein one or more diagnostic tests are subsequently performed remotely from the tool based on transmission of the one or more grip metrics.

Figure 4A:
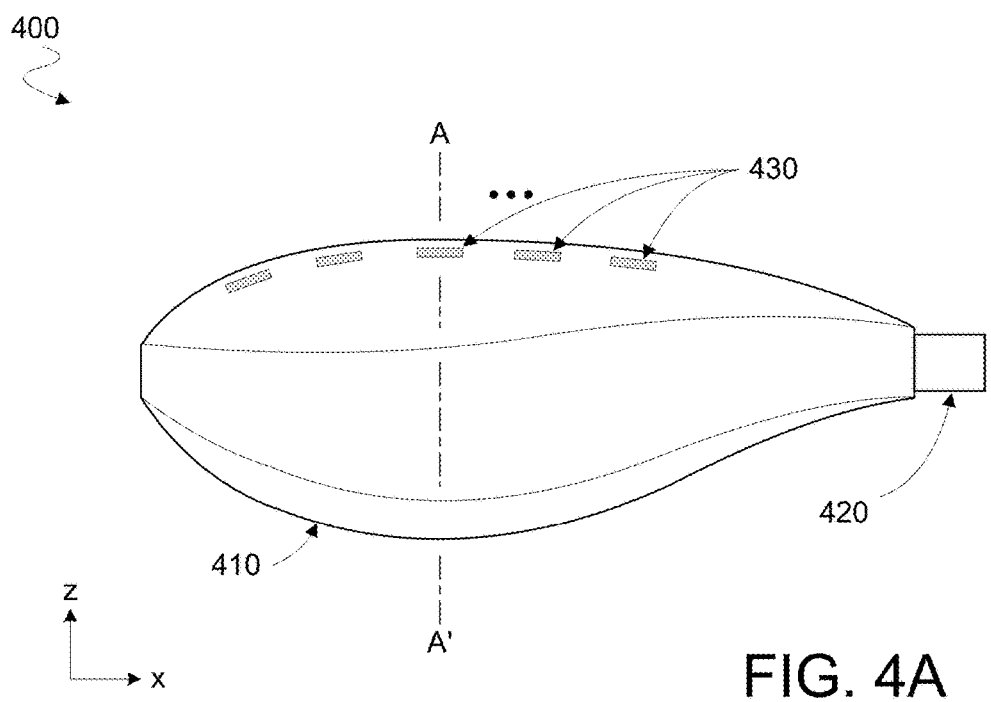
FIG. 4A is a perspective view illustration of the handheld tool that evaluates user grip, in accordance with an embodiment of the disclosure.

FIG. 4A illustrates elements of a tool 400 including circuit logic to determine grip metric information according to an embodiment. Tool 400 may include, for example, one or more features of handheld tool 100—e.g., where tool 400 includes GEM 200. In one embodiment, tool 400 includes circuitry to perform some or all of method 300.

As shown in FIG. 4A, tool 400 may include a housing 410—such as housing 102, for example—to serve as a handle for a user to grab. Tool 400 may further comprise an attachment arm 420 to receive, or otherwise couple tool 400 to, a user-assistive device (not shown). The user-assistive device may aid in any of a wide variety of eating, personal hygiene and/or other tasks. By way of illustration and not limitation, attachment arm 420 may receive an attachment comprising an eating utensil, hairbrush, toothbrush, comb, screwdriver head, socket or the like. Embodiments, such as that of tool 400, variously provide for measurement of grip strength from a handle (e.g., housing 410) of an instrumented tool, and the tracking of one or more grip characteristics over time as a means to assess the severity of a medical condition such as Parkinson's disease.

In the illustrative embodiment shown, tool 400 is instrumented with pressure sensitive sensors 430 that, for example, are variously positioned in or on housing 410 along a length (x-axis) of tool 400. Sensors 430 may be used to assess grip strength during daily use of tool 400 by a user or during a dedicated grip measurement test period. Recording and logging of information based on grip pressure measurements may be used—e.g., at tool 400 or a remote device—to assess disease progression. The particular number and distribution of sensors 430 is merely illustrative, and is not limiting on other embodiments comprising fewer, more and/or differently arranged pressure sensors.

Figure 4B:
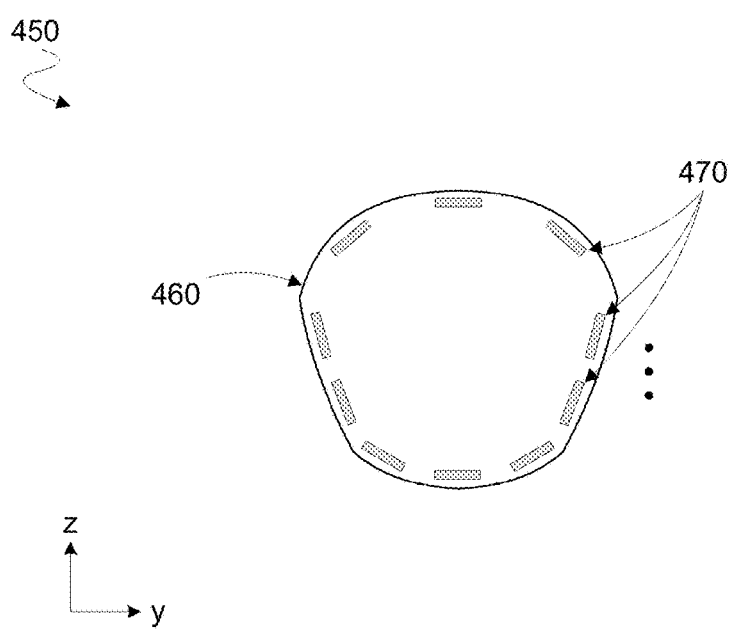
FIG. 4B is a cross-sectional view illustration of the handheld tool that provides diagnostic evaluation of user grip, in accordance with an embodiment of the disclosure.

FIG. 4B illustrates in a cross-sectional view an arrangement of pressure sensors 470 in a housing 460 of a tool 450 configured to determine grip metric information according to an embodiment. In an embodiment, tool 450 includes some or all of the features of tool 400. For example, FIG. 4B may be a cross-sectional view of tool 400 in the z-y plane such as plane A-A' shown in FIG. 4A. As shown in FIG. 4B, some or all of pressure sensors 470 may be variously arranged around a periphery of housing 460—e.g., in addition to or instead of being distributed along a length of housing 460. The particular number and distribution of sensors 470 is merely illustrative, and is not limiting on other embodiments comprising fewer, more and/or differently arranged pressure sensors.

Figure 5A:
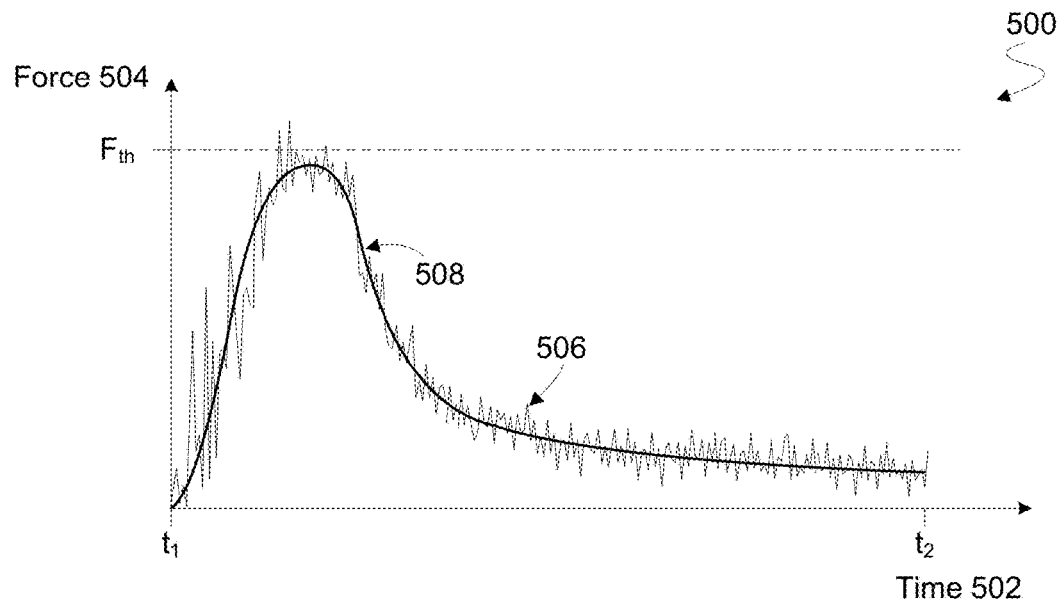
FIGS. 5A, 5B are graphs each illustrating a respective grip evaluation performed according to a corresponding embodiment of the disclosure.
Figure 5B:
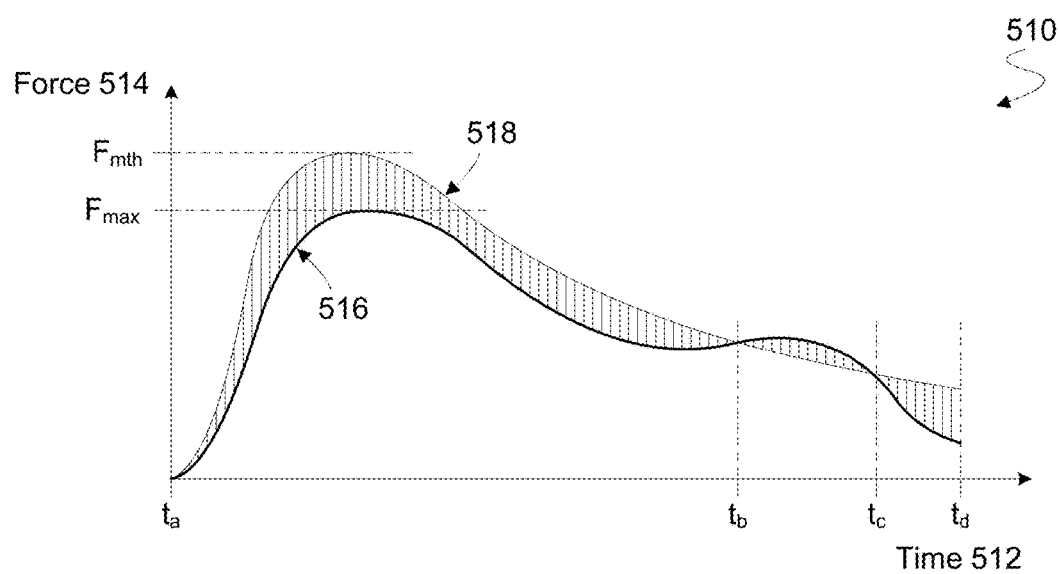

FIGS. 5A, 5B show graphs 500, 510 representing evaluations, each according to a respective embodiment, to detect for one or more grip characteristics that are indicative of a state of a medical disorder. To illustrate certain features of various embodiments, graphs 500, 510 are described herein with reference to evaluation of grip force. However, such description may be extended to additionally or alternatively apply to any of a variety of other evaluations of grip characteristics to determine medical diagnostic information.

Graph 500 includes values over time 502 of a force 504 applied to a handle of a tool according to an embodiment (e.g., handheld tool 100). Graph 500 includes a plot 506 of points representing raw data from one or more pressure sensors of the tool. Plot 506 may include data from multiple sensors or a single sensor that, for example, is selected from among multiple sensors based on that single sensor being identified as outputting a most relevant (e.g., largest magnitude) set of sensor data.

Evaluation of grip metric information may include determining a mean, average or other statistical calculation based on plot 506, such as the illustrative running average values represented by plot 508. Alternatively or in addition, evaluation of grip metric information may include performing a comparison based sensor data and reference information identifying one or more diagnostic test criteria. By way of illustration and not limitation, plot 506 and/or plot 508 may be evaluated to determine whether user grip exceeded a threshold grip force level $F_{th}$. In some embodiments, a diagnostic test includes determining whether user grip exceeded $F_{th}$ for at least some threshold period of time. Other tests to evaluate user grip may include determining whether spasm, tremor or other unintentional muscle movement is indicated—e.g., based on frequency analysis of plot 506 and/or plot 508.

Graph 510 of FIG. 5B includes values over time 512 of a force 514 applied to a handle of a tool according to an embodiment. Graph 500 includes a plot 516 that, for example, represents a running average (or other statistically processed version) of pressure sensor information generated at the tool. In one embodiment, plots 506, 508 represent a result of a test wherein a user of the tool is prompted (e.g., by the tool itself or by some other device communicatively coupled to the tool) to exert a maximum burst grip pressure—e.g., without the user sustaining such pressure. By contrast, plot 516 may represent a result of a test wherein the tool user is prompted to sustain at least some minimum level of grip pressure for an extended period of time.

In order to perform a diagnostic test of user grip, plot 516 may be evaluated based on information that specifies or otherwise indicates a reference plot 518 of grip force. In the illustrative scenario shown, reference plot 518 corresponds to a test lasting in duration from a time $t_a$ to a time $t_d$, where the user's grip managed to be above reference plot 518 only during a period between time $t_b$ and time $t_c$. Reference plot 518 may provide a basis of comparison for evaluating plot 516. For example, a maximum force level $F_{max}$ of plot 516 may be compared to a threshold maximum force level $F_{mth}$ to determine whether a user's maximum grip strength is symptomatic of advancing Parkinson's disease. Alternatively or in addition, an advancing medical condition (such as Parkinson's disease) may be indicated by a difference between an area under plot 518 and an area under plot 516 being greater than some threshold amount. Reference information such as that representing $F_{th}$, curve 518, $F_{mth}$, threshold amounts and/or other reference values may be provided a priori by a clinician or other remote agent—e.g., where the reference information is determined based at least in part on population statistics, evaluation of the user in a clinic setting and/or the like.

Techniques and mechanisms for determining diagnosis information with a handheld tool are described herein. In the above description, for purposes of explanation, numerous specific details are set forth in order to provide a thorough understanding of certain embodiments. It will be apparent, however, to one skilled in the art that certain embodiments can be practiced without these specific details. In other instances, structures and devices are shown in block diagram form in order to avoid obscuring the description.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the detailed description herein are presented in terms of algorithms and symbolic representations of operations on data bits within a computer memory. These algorithmic descriptions and representations are the means used by those skilled in the computing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Certain embodiments also relate to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs) such as dynamic RAM (DRAM), EPROMs, EEPROMs, magnetic or optical cards, or any type of media suitable for storing electronic instructions, and coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description herein. In addition, certain embodiments are not described with reference to any particular programming language. It will be appreciated that a variety of programming languages may be used to implement the teachings of such embodiments as described herein.

Besides what is described herein, various modifications may be made to the disclosed embodiments and implementations thereof without departing from their scope. Therefore, the illustrations and examples herein should be construed in an illustrative, and not a restrictive sense. The scope of the invention should be measured solely by reference to the claims that follow.

What is claimed is:

1. A tool, comprising:
   a handle;
   an attachment arm extending from the handle and having a distal end configured to accept and hold a user-assistive device;
   one or more sensors disposed within the handle, the one or more sensors configured to sense a pressure exerted on the handle by a hand of a user while a user-assistive device is coupled to the distal end of the attachment arm;

a memory disposed within the handle;

grip evaluation logic coupled to the one or more sensors to receive from the one or more sensors an output indicative of the pressure, the grip evaluation logic comprising circuitry configured to calculate a grip metric based on the output and further configured to record into the memory a plurality of grip metrics acquired over time along with a type of the user-assistive device coupled to the distal end of the attachment arm for each of the grip metrics; and a communication interface coupled to the grip evaluation logic, the communication interface configured to output from the tool a signal including medical diagnostic information based on the grip metric.

2. The tool of claim 1, wherein the grip metric indicates whether a threshold amount of grip force has been applied to the handle.

3. The tool of claim 2, wherein the grip metric indicates whether the threshold amount of grip force has been applied to the handle for a threshold period of time.

4. The tool of claim 1, the communication interface further to generate a prompt to indicate that the user is to perform a grip action of a diagnostic test.

5. The tool of claim 1, the grip evaluation logic further to evaluate the grip metric based on reference information including one or more threshold values of a diagnostic test criteria.

6. The tool of claim 1, the communication interface to send the signal from the tool to a remote device via a network, wherein based on the signal, the remote device performs a diagnostic test to evaluate the user.

7. The tool of claim 1, wherein the user-assistive device comprises a kitchen utensil.

8. The tool of claim 1, wherein the user-assistive device comprises an attachment to perform a personal hygiene task.

9. The tool of claim 1, wherein the user assistive device comprises one of a kitchen utensil, a personal grooming tool, or a personal hygiene tool for performing a personal task including at least one of eating, grooming, or makeup application, and wherein the one or more sensors are positioned within the handle to sense the pressure while the personal task is performed by the user.

10. The tool of claim 1, wherein the grip metrics include one or more of a rate of change of grip pressure, a frequency of grip pulses, or a duration of each grip.

11. The tool of claim 1, wherein the grip evaluation logic further comprises circuitry configured to record a time stamp into the log with each of the plurality of grip metrics acquired over time.

12. The tool of claim 1, wherein the grip evaluation logic further comprises circuitry configured to record a type of a task performed by the user with the user-assistive device while recording the grip metrics.

13. A method performed by a tool, the method comprising:

sensing a pressure exerted on a handle of the tool by a hand of a user while a user-assistive device is coupled to a distal end of an attachment arm of the tool;

calculating a grip metric based on the pressure;

storing the grip metric to a log of the tool;

determining a type of the user-assistive device coupled to the distal end of the attachment arm while sensing the pressure;

storing the type of the user-assistive device with the grip metric to the log; and transmitting from the tool a signal including medical diagnostic information based on the grip metric and the type of the user-assistive device.

14. The method of claim 13, wherein the grip metric indicates whether a threshold amount of grip force has been applied to the handle.

15. The method of claim 14, wherein the grip metric indicates whether the threshold amount of grip force has been applied to the handle for a threshold period of time.

16. The method of claim 13, further comprising generating a prompt indicating that the user is to perform a grip action of a diagnostic test.

17. The method of claim 13, further comprising evaluating the grip metric based on reference information including one or more threshold values of a diagnostic test criteria.

18. The method of claim 13, wherein the signal is sent from the tool to a remote device via a network, wherein based on the signal, the remote device performs a diagnostic test to evaluate the user.

19. The method of claim 13, wherein the user-assistive device comprises a kitchen utensil.

20. A non-transitory computer-readable storage medium having stored thereon instructions which, when executed by one or more processing units, cause a tool to perform a method comprising:

sensing a pressure exerted on a handle of the tool by a hand of a user while a user-assistive device is coupled to a distal end of an attachment arm of the tool;

calculating a grip metric based on the pressure;

storing the grip metric to a log of the tool;

determining a type of the user-assistive device coupled to the distal end of the attachment arm while sensing the pressure;

storing the type of the user-assistive device with the grip metric to the log; and transmitting from the tool a signal including medical diagnostic information based on the grip metric and the type of the user-assistive device.

21. The computer-readable storage medium of claim 20, wherein the grip metric indicates whether a threshold amount of grip force has been applied to the handle.

22. The computer-readable storage medium of claim 20, the method further comprising generating a prompt indicating that the user is to perform a grip action of a diagnostic test.

23. The computer-readable storage medium of claim 20, the method further comprising evaluating the grip metric based on reference information including one or more threshold values of a diagnostic test criteria.

24. The computer-readable storage medium of claim 20, wherein the user-assistive device comprises a kitchen utensil.

* * * * *